(12) United States Patent
Nace

(10) Patent No.: US 10,744,021 B1
(45) Date of Patent: Aug. 18, 2020

(54) DEVICE FOR, AND METHOD OF, PROTECTING KNEES FROM EXTERNAL FORCES

(71) Applicant: Richard Nace, Pinellas Park, FL (US)

(72) Inventor: Richard Nace, San Jose (CR)

(*) Notice: Subject to any disclaimer, the term of this patent is extended or adjusted under 35 U.S.C. 154(b) by 1 day.

(21) Appl. No.: 16/415,195

(22) Filed: May 17, 2019

(51) Int. Cl.
*A61F 5/01* (2006.01)

(52) U.S. Cl.
CPC ........... *A61F 5/0123* (2013.01); *A61F 5/012* (2013.01); *A61F 2005/0165* (2013.01); *A61F 2005/0172* (2013.01)

(58) Field of Classification Search
CPC .......... A61F 5/012; A61F 5/0123; A61F 5/34; A61F 5/0106; A61F 5/0125; A61F 2005/0169; A61F 2005/0179
USPC .................................... 602/5, 13, 16, 23, 26
See application file for complete search history.

(56) References Cited

U.S. PATENT DOCUMENTS

| | | | | |
|---|---|---|---|---|
| 2,150,290 A | * | 3/1939 | Mulvey | A42B 3/12 2/413 |
| 4,854,308 A | * | 8/1989 | Drillio | A61F 5/0123 602/16 |
| 5,707,347 A | * | 1/1998 | Bixler | A61F 5/0125 602/16 |
| 10,085,869 B2 | * | 10/2018 | Nace | A61F 5/012 |
| 2014/0276250 A1 | * | 9/2014 | Branch | A61H 1/008 601/5 |

* cited by examiner

*Primary Examiner* — Anna K Kinsaul
*Assistant Examiner* — Caitlin A Carreiro
(74) *Attorney, Agent, or Firm* — Larson & Larson, P.A.; Justin P. Miller; Frank Liebenow

(57) ABSTRACT

The solution to protecting the human knee from external forces is to surround the knee with a brace that includes adjustable air bladders to absorb external forces before the external forces pass into the knee and cause internal knee injury. Such a brace includes a pair of struts that are bifurcated by hinges, the adjustable air bladders placed between the knee and the hinges.

9 Claims, 9 Drawing Sheets

DEVICE FOR, AND METHOD OF, PROTECTING KNEES FROM EXTERNAL FORCES

FIELD

This invention relates to the field of braces and more particularly to lower-leg brace that shields the knee from external forces.

BACKGROUND

Knees are subject to tremendous outside forces. As a joint centered in the leg, with long bones both above and below, the knee is readily damaged. A force against the side of the knee, which would cause no harm if applied to the hip or ankle, can readily tear internal knee ligaments. A rotational force carried through the ankle and hip without harm can cause internal knee rotation, snapping the ligaments that create knee stability.

The forces described above are an issue in sports, such as football, where external forces are frequently applied to the side of a player's leg. And where twisting is common due to stops, starts, and turns, with cleats preventing the foot from releasing and turning with the body.

What is needed is a device and method for protecting a knee from the external forces that cause internal damage.

SUMMARY

The solution to protecting the human knee from external forces is to surround the knee with a brace that includes adjustable air bladders to absorb external forces before the external forces pass into the knee and cause internal knee injury. Such a brace includes a pair of struts that are bifurcated by hinges, the adjustable air bladders placed between the knee and the hinges.

A first failure mode for a knee is buckling, or a sideways deflection, caused by a load applied to the side of the knee. Specifically, a side load is applied to the knee, with the foot braced against the ground, and the player's body weight bracing the hip position. The knee is pushed in from the side, as the ankle and hip move little.

A force against the inside the knee will likely damage the outside ligament, the Lateral Collateral Ligament (LCL). A force against the outside of the knee will likely damage the ligament on the inside of the knee, the Medial Collateral Ligament (MCL). Such damage occurs during, for example, a side tackle of a player's leg.

A second failure mode for a leg is twisting. The foot is static with respect to the ground, and the body twists. The static lower leg and rotating upper leg meet at the knee, with the anterior cruciate ligament (ACL) required to bear the load. If the twisting is excessive, the ACL will likely tear. This is caused by, for example, a front off-center tackle.

A third failure mode is overextension. The fully-extended position of the lower leg with respect to the upper leg is 180 degrees. During an activity, such as soccer, a player's lower leg may be pinned in place by another player, but the upper leg may remain in motion as the players body continues forward. The result is a forward over-extension of the knee, likely damaging the posterior cruciate ligament (PCL).

Preventing these knee failure modes is required for protection of the knee joint, and thus continued participation in sports.

The solution is a knee brace that can carry loads from the lower leg to the upper leg, and the upper leg to the lower leg, without reliance on the knee joint. Additionally, a knee brace that uses air bladders between the knee and brace structure, where an external force triggers a compression cycle within the air bladder. The compression cycle dissipates the compressive force before it can affect the knee.

The air bladders are inflatable pouches that hold air, under pressure, to create a force against adjacent objects. The air bladders have inlet/outlet nozzles to allow a user to increase or decrease the pressure of the contained air, thereby adjusting the rigidity of the air bladder.

Additionally, an opposing bladder supports the opposite side of the knee, preventing outward deflection that causes ligament damage.

Static pads on either side of the knee joint—also referred to as condyle pads—lack the ability to enter a compression cycle like an air bladder can. As a result, any external force is passed into the knee joint, potentially causing harm.

In contrast, air bladders act to dissipate load, as well as to contain the leg bones. Inflation of the medial and lateral pneumatic bladders locks the in-and-out position of the knee, avoiding sideways motion.

The medial and lateral bladders act as shock absorbers, dampening the violent effects of a lateral or a medial force applied to the knee joint.

When an external force on the lateral bladder occurs, such as by impact, the incoming energy is dampened by a rapid cycle of compression and decompression before reaching the knee joint.

The result is partial shock absorption, reducing the impact that makes it through to the knee.

For example, the knee joint may experience a varus, or inward force, that would normally push the knee joint into a bow-leg position. Instead, the inflated lateral bladder will absorb a portion of the force, and slow the movement of the knee, thus reducing risk of stretching injury to medial collateral ligament (MCL).

In case of valgus thrust the medial bladder performs the same function and reduces risk of lateral collateral ligament (LCL) tear.

In addition to the air bladders, elastic members on either side of the knee add stability in extension. Due to the structure of the knee and its musculature, the knee joint is inherently rotatably stable in extension but it lacks such stability in flexion.

The disclosed brace used this its advantage by applying an extension torque on the knee, creating the stability of extension even when the join is in flexion.

The disclosed knee brace uses a swing assist system to help the patient achieve full extension, and thus the proper heel-to-toe gait. The swing assist system includes an energy storage member that extends across the hinge, connecting the upper portion of the support arm to the lower portion of the support arm. The energy storage member gathers energy during flexion of the knee joint and releases it during extension. The result is an improvement in leg extension, even for patients who lack the strength or conditioning to achieve full leg extension in the absence of the disclosed knee brace.

The swing assist system is installed on one or both of the hinges. There is no requirement that both hinges have a swing assist system, although such an arrangement is likely to produce the most balanced force during extension and flexion of the knee brace.

The energy storage member of the swing assist system is any device capable of repeatedly storing and releasing rotational energy. Such devices include elastic/rubber bands, elastic/rubber loops, O-rings, cylindrical cord stock, torsion springs, coil springs, and all other similar devices.

The energy storage member attaches to the strut above and below the hinge, or to an extension of the strut above and below the hinge. The energy storage member location relative to the hinge is dependent on the location from which it can best provide energy storage and return. If the energy storage member is an elastic band, it is likely best located on the anterior side of the hinge. If it is a coil spring that is to be extended during flexion, then it is best located on the anterior side of the hinge. If it is a coil spring to be compressed during flexion, it is best located on the posterior side of the hinge.

Energy storage members that store energy through rotation are likely best located at the rotational center of the hinge.

Returning to the air bladders, if there is internal knee damage, such as general cartilage deterioration, a bladder is needed at both the medial and lateral locations of the leg. Providing simultaneous external forces against both sides of the knee joint unloads the knee joint, creating space between the cartilage surfaces.

Compression of both sides of the knee "distracts" the knee joint. The pressure lifts the femur, creating space in the joint. The pressure acts to stretch the top of the tibia away from the base of the femur. A shock-absorption effect is created by the presence of new space. With the new space in the knee joint, cartilage begins to grow. This new cartilage in turn decreases joint pain and improves function. The space also takes up any laxity in the ligaments, increasing knee stability.

For users with a compromised MCL or LCL, differential inflation of the air bladders is also an option. Differential inflation is inflating one bladder more than its opposing bladder, pushing the knee toward the underinflated bladder.

If the knee is carrying its load on the medial side, the knee joint has rolled toward the medial surfaces. This creates space within the lateral side of the knee. Applying force using an air bladder to the lateral side rolls the knee joint toward the lateral side of the knee, creating space in the knee joint.

Correspondingly, if the knee is carrying its load on the lateral side, the knee joint has rolled toward the lateral surfaces. This creates space within the medial side of the knee. Applying force using an air bladder to the medial side rolls the knee joint toward to medial side of the knee, creating space in the knee joint.

For the brace to have the desired effect, it must be correctly worn. The steps of applying the brace are as follows:
1. Open the rear straps of the brace;
2. Place the brace over the lower leg, centering the hinges on the knee joint;
3. Close the rear straps;
4. Tighten all straps to create a snug fit;
5. Inflate medial bladder until snug;
6. Inflate lateral bladder until snug;
7. Inflate lateral bladder by one to two additional pumps to move from snug fit to tight fit; and
8. Inflate medial bladder by one to two additional pumps to move from snug fit to tight fit.

Discussion now moves to a detailed description of one embodiment, and associated method, that acts to protect a knee joint.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
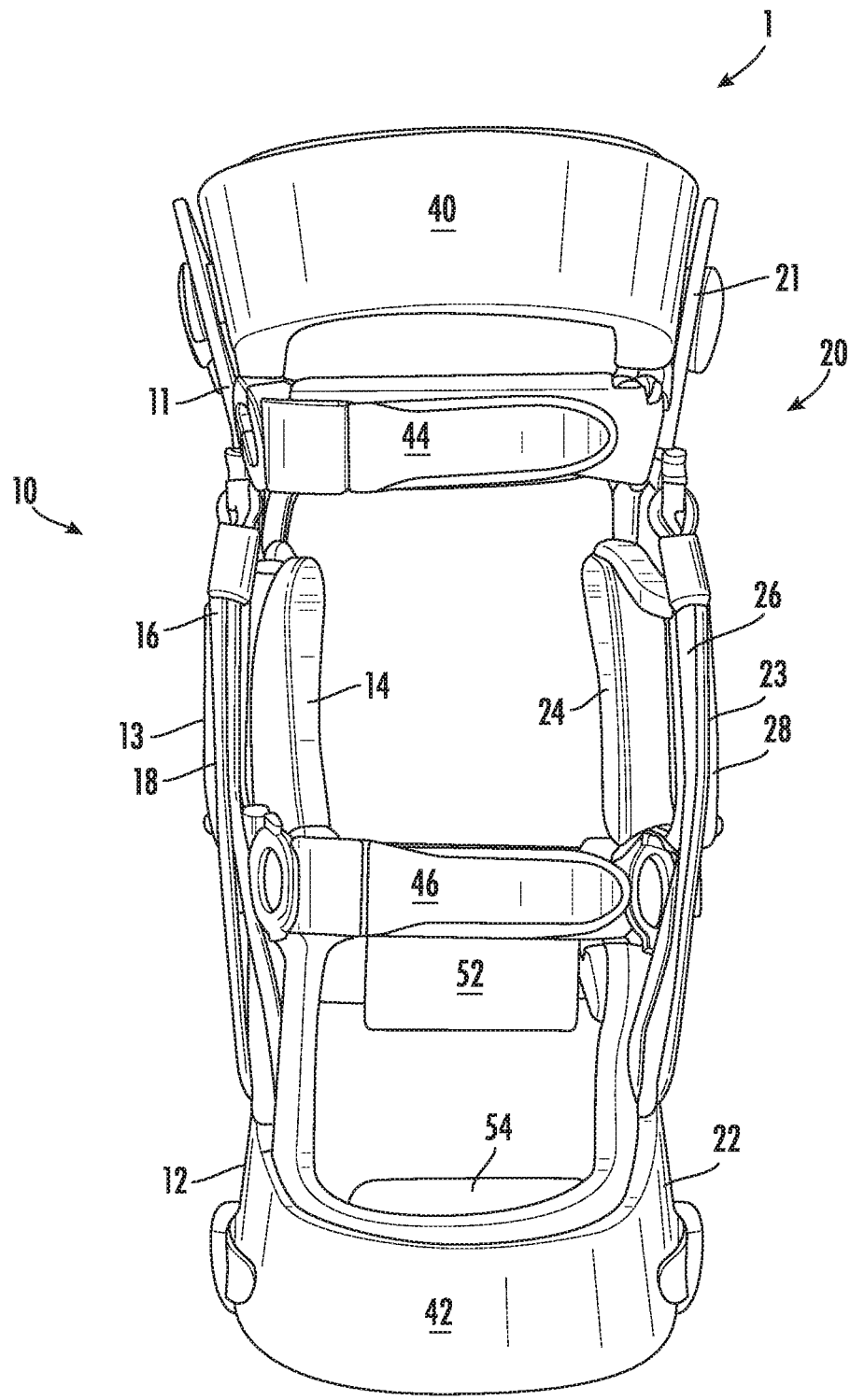
FIG. 1 illustrates a front view of the device for protecting a knee from external forces.
Figure 2:
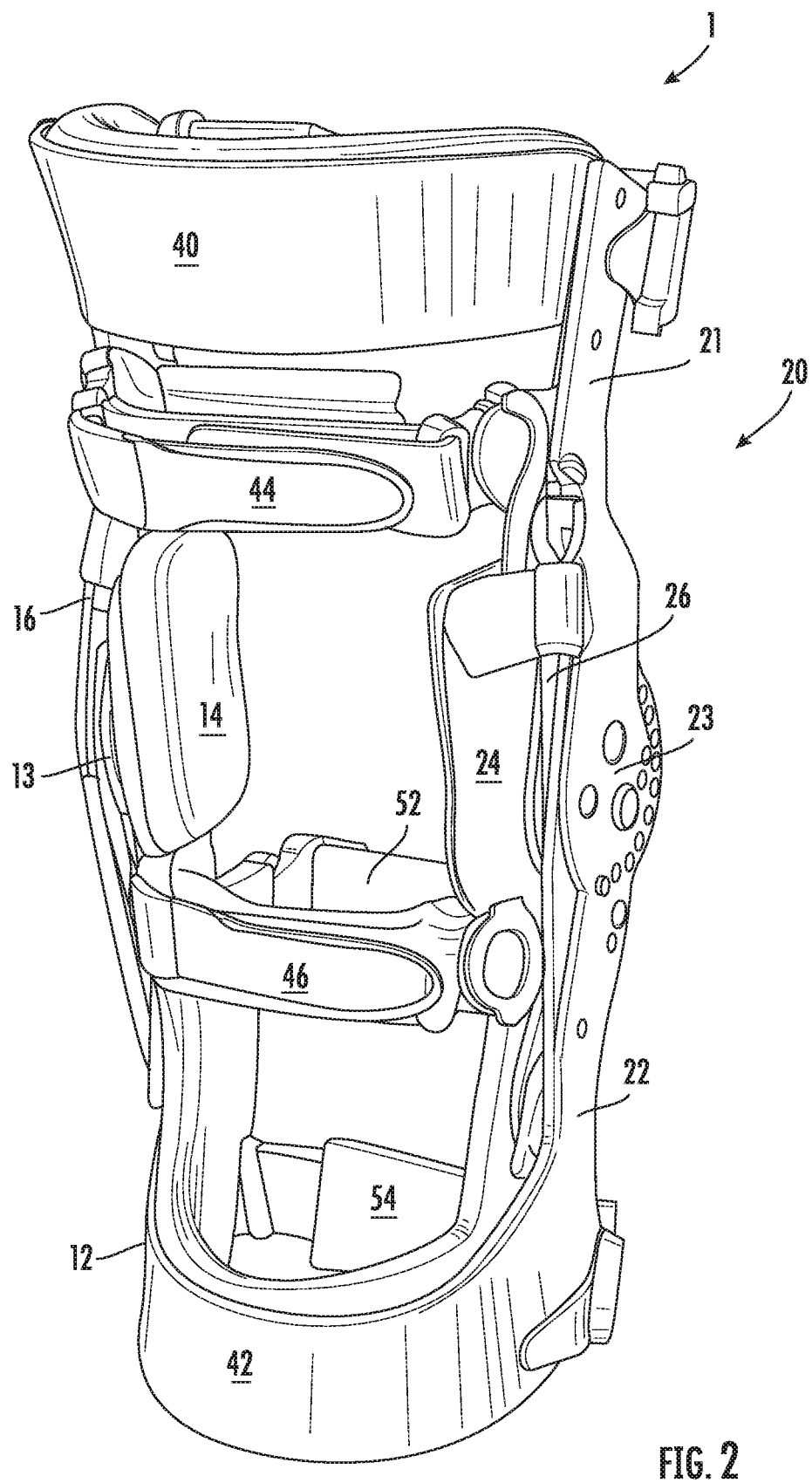
FIG. 2 illustrates an isometric view of the device for protecting a knee from external forces.
Figure 3:
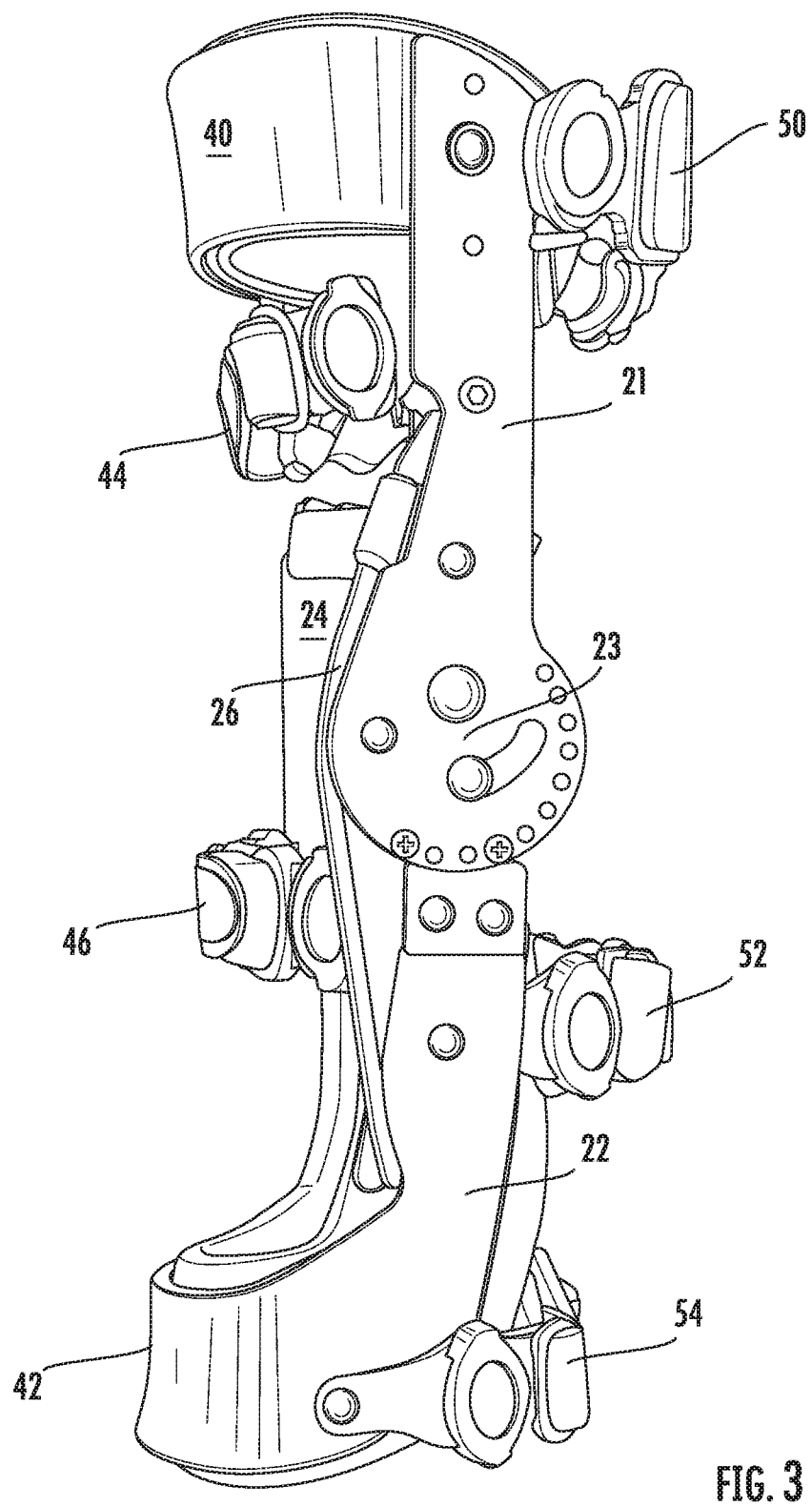
FIG. 3 illustrates a side view of the device for protecting a knee from external forces.
Figure 4:
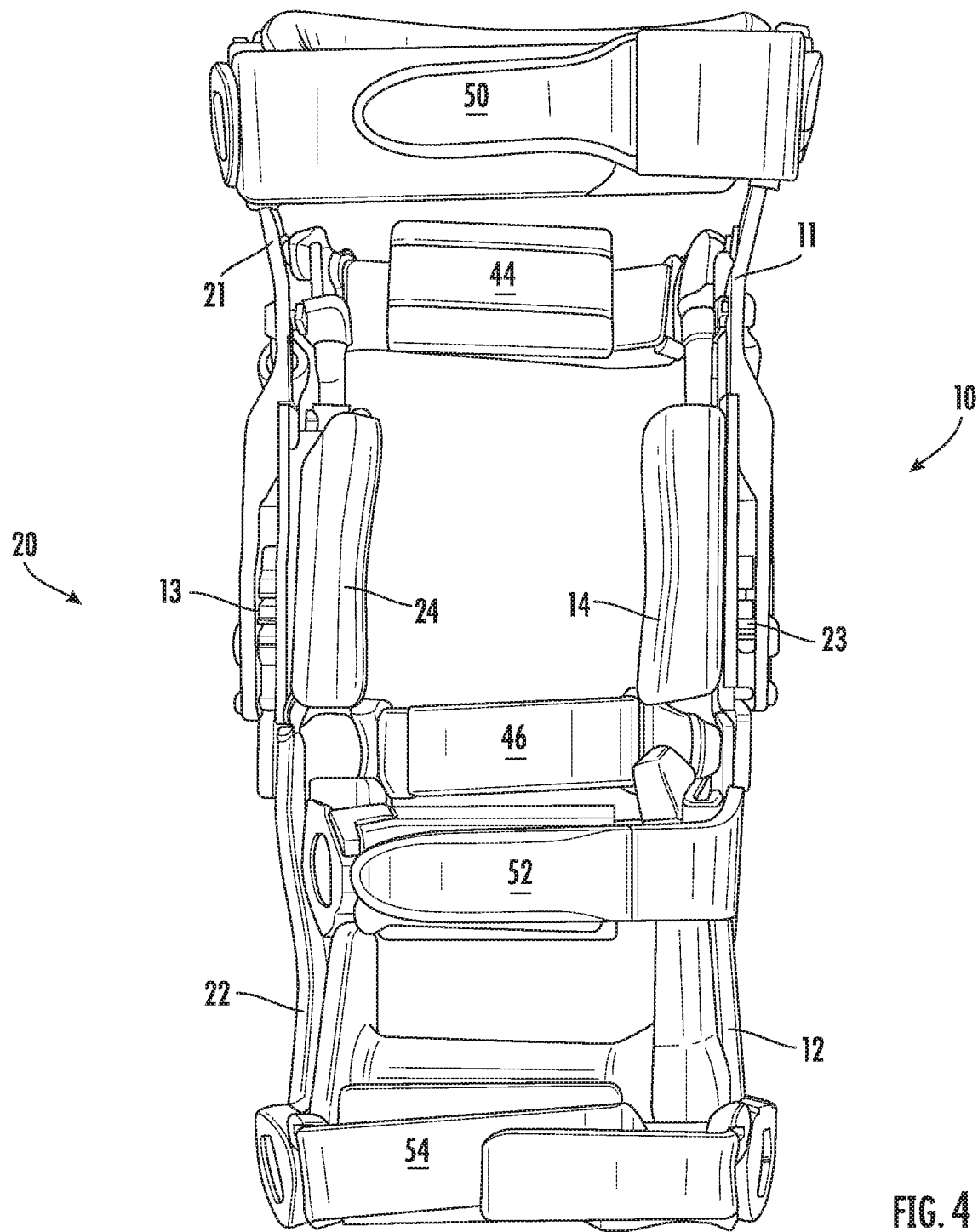
FIG. 4 illustrates a rear view of the device for protecting a knee from external forces.

Reference will now be made in detail to the presently preferred embodiments of the invention, examples of which are illustrated in the accompanying drawings. Throughout the following detailed description, the same reference numerals refer to the same elements in all figures.

Referring to FIG. 1-4, front, isometric, side, and rear views are shown of the device for protecting a knee from external forces.

The force dissipation brace 1 includes a lateral strut 10 and medial strut 20.

The lateral strut 10 is formed from a lateral upper segment 11 and lateral lower segment 12 that meet at lateral hinge 13. A lateral bladder 14 separates the lateral hinge 13 from the knee 102 (see FIG. 8).

A lateral elastic member 16 connects lateral upper segment 11 and lateral lower segment 12 across lateral hinge, the lateral elastic member 16 held within lateral guide channel 18.

The medial strut 20 is formed from a medial upper segment 21 and medial lower segment 22 that meet at medial hinge 23. A medial bladder 24 separates the medial hinge 23 from the knee 102 (see FIG. 8).

A medial elastic member 26 connects medial upper segment 22 and medial lower segment 22 across medial hinge 23, the medial elastic member 26 held within medial guide channel 28.

The force dissipation brace 1 encloses the front of the lower leg 100 (see FIG. 8) using fixed-length anterior thigh cuff 40 and anterior shin cuff 42, and adjustable-length anterior thigh strap 44 with anterior shin strap 46.

The force dissipation brace encloses the back of the lower leg 100 (see FIG. 8) using adjustable-length posterior thigh strap 50, posterior upper shin strap 52, and posterior lower shin strap 54.

Figure 5:
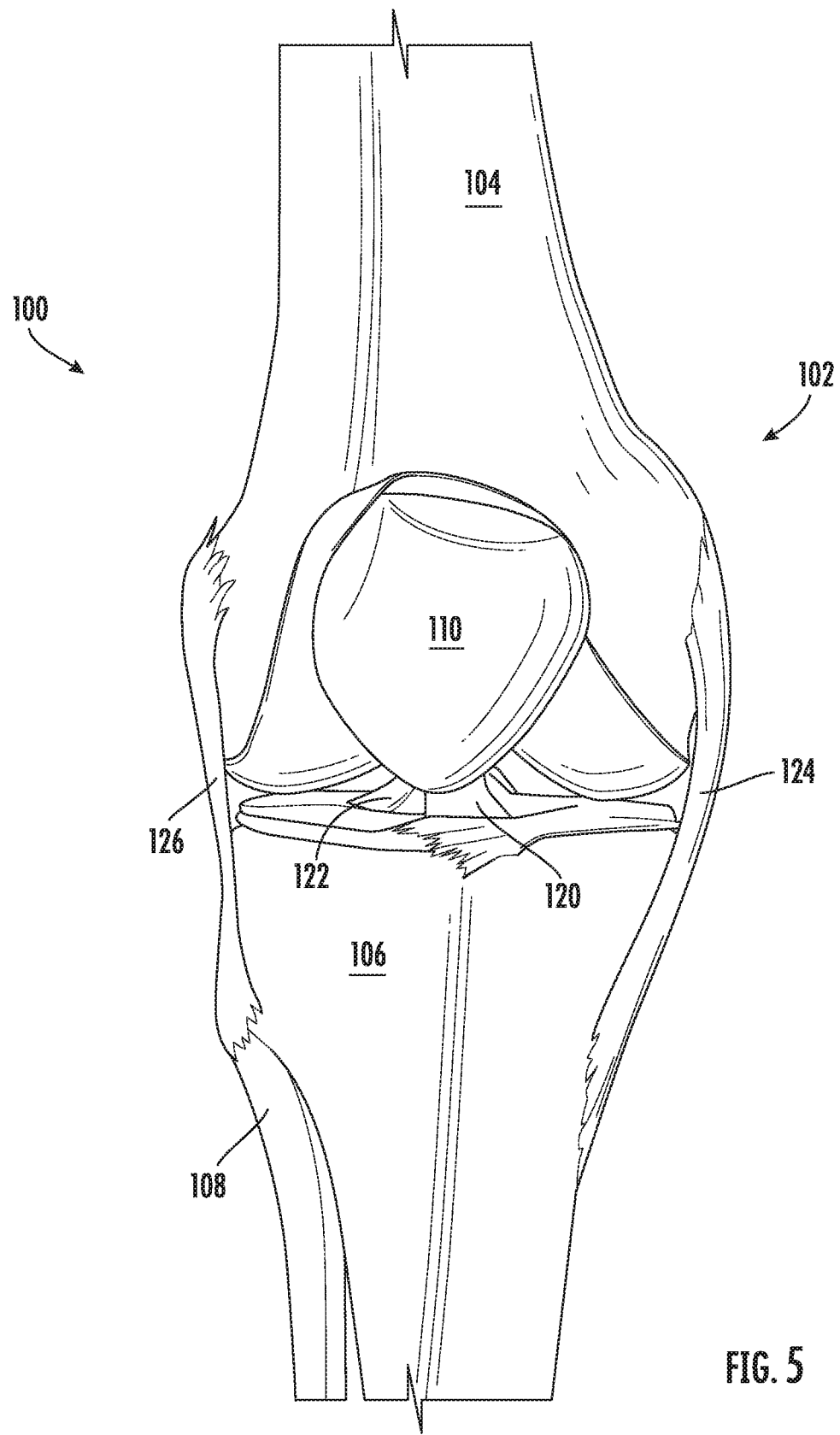
FIG. 5 illustrates a view of an undamaged knee.

Referring to FIG. 5, a view of an undamaged knee is shown.

The lower leg 100, formed from femur 104, tibia 106, and fibula 108 is divided by knee 102. The knee 102 is protected by a patella (knee cap) 110.

Crossing the knee are multiple ligaments. Internal to the knee 102 are ACL 120 and PCL 122. On the inside of the knee 102 is MCL 124, and on the outside of the knee 102 is LCL 126.

Figure 6:
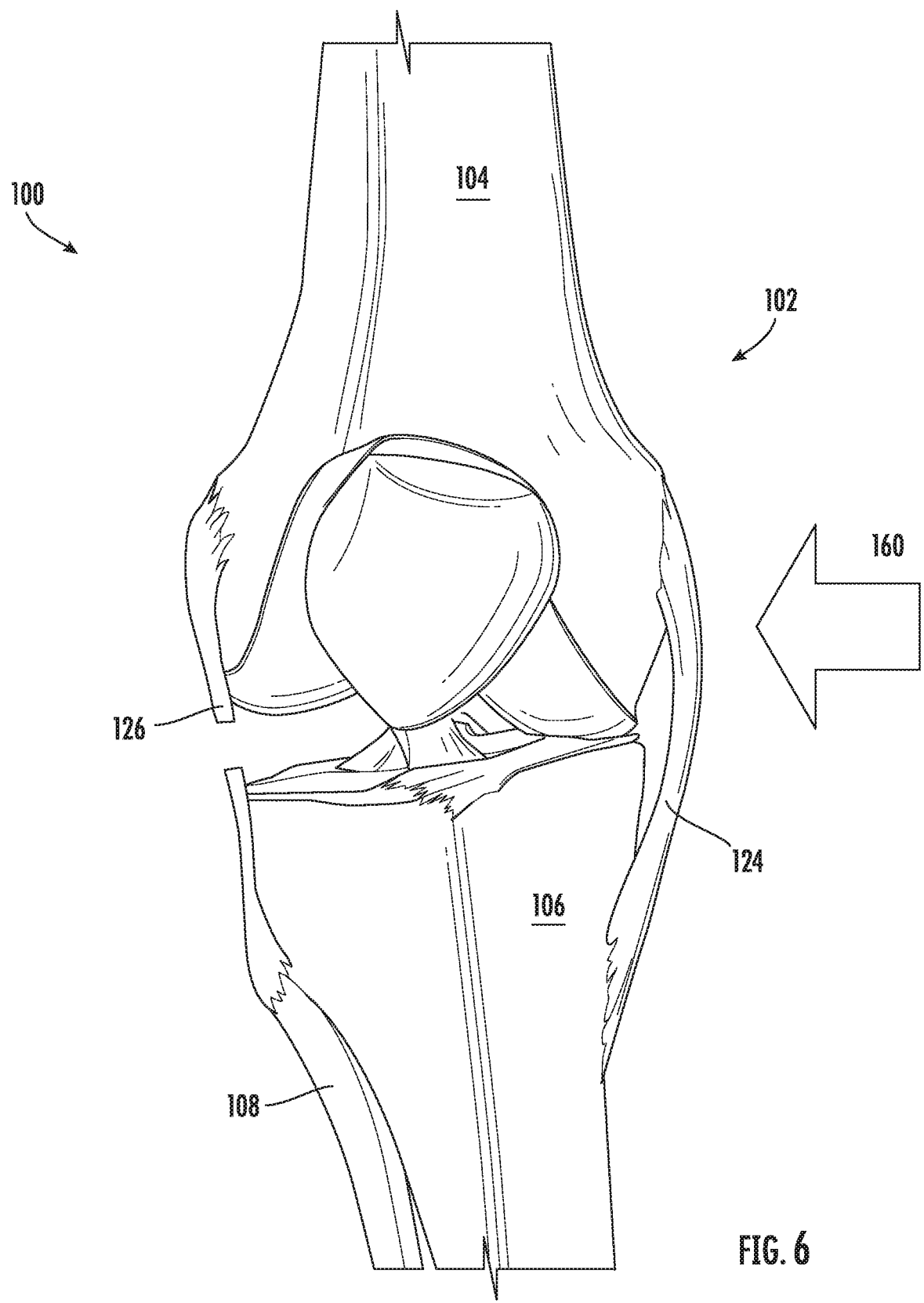
FIG. 6 illustrates a view of a knee with an LCL tear.

Referring to FIG. 6, a view of a knee with an LCL tear is shown.

Again shown are lower leg 100 formed from femur 104, tibia 106, and fibula 108, divided by knee 102.

MCL 124 and LCL 126 are placed at either side of the knee 102.

A medial force 160 against the knee 102 causes stretching on the opposite side of the knee, stretching the LCL 126 and causing a tear.

Figure 7:
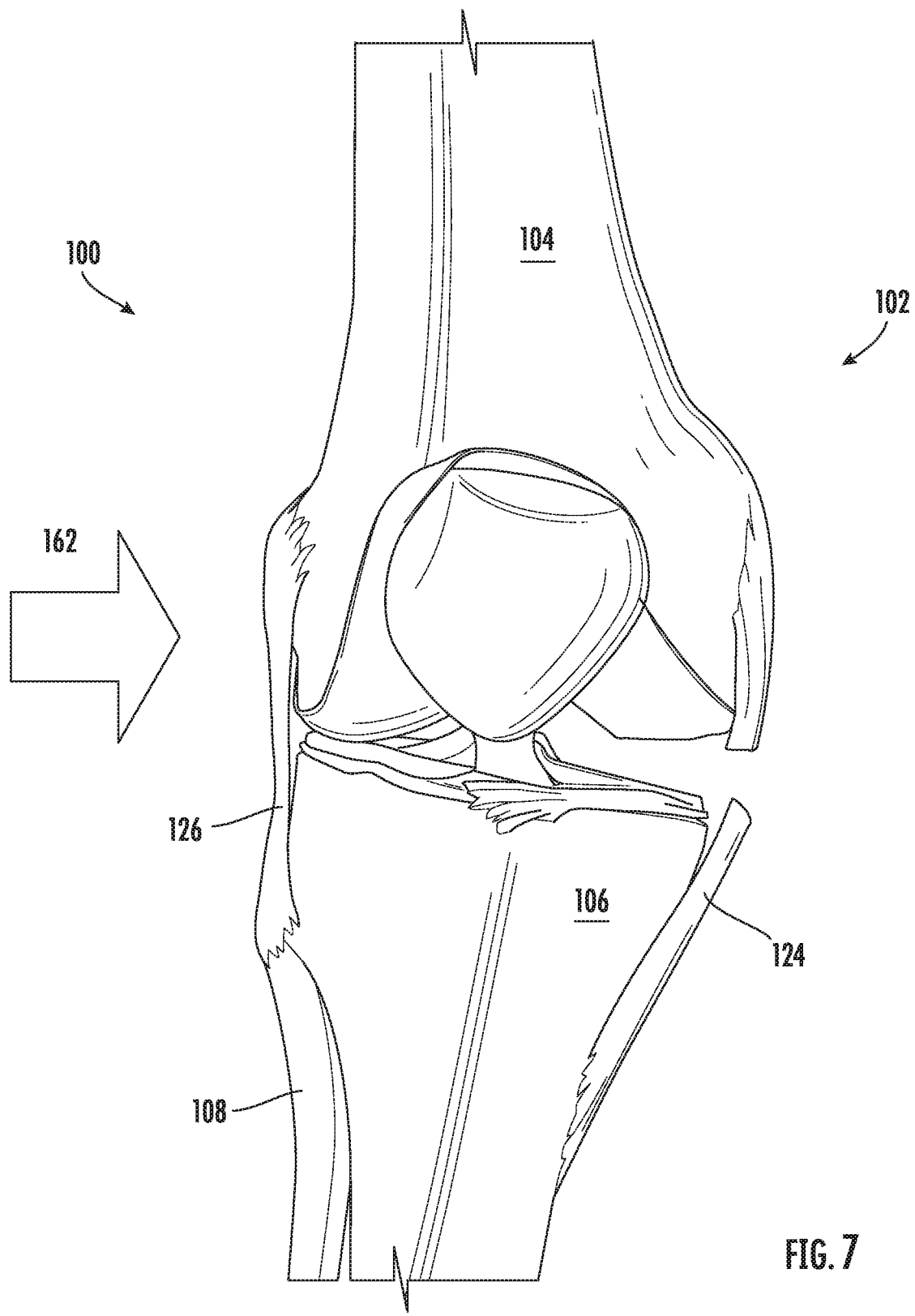
FIG. 7 illustrates a view of a knee with an MCL tear.

Referring to FIG. 7, a view of a knee with an MCL tear is shown.

Again shown are lower leg 100 formed from femur 104, tibia 106, and fibula 108, divided by knee 102.

MCL 124 and LCL 126 are placed at either side of the knee 102.

A lateral force 162 against the knee 102 causes stretching on the opposite side of the knee, stretching the MCL 124 and causing a tear.

Figure 8:
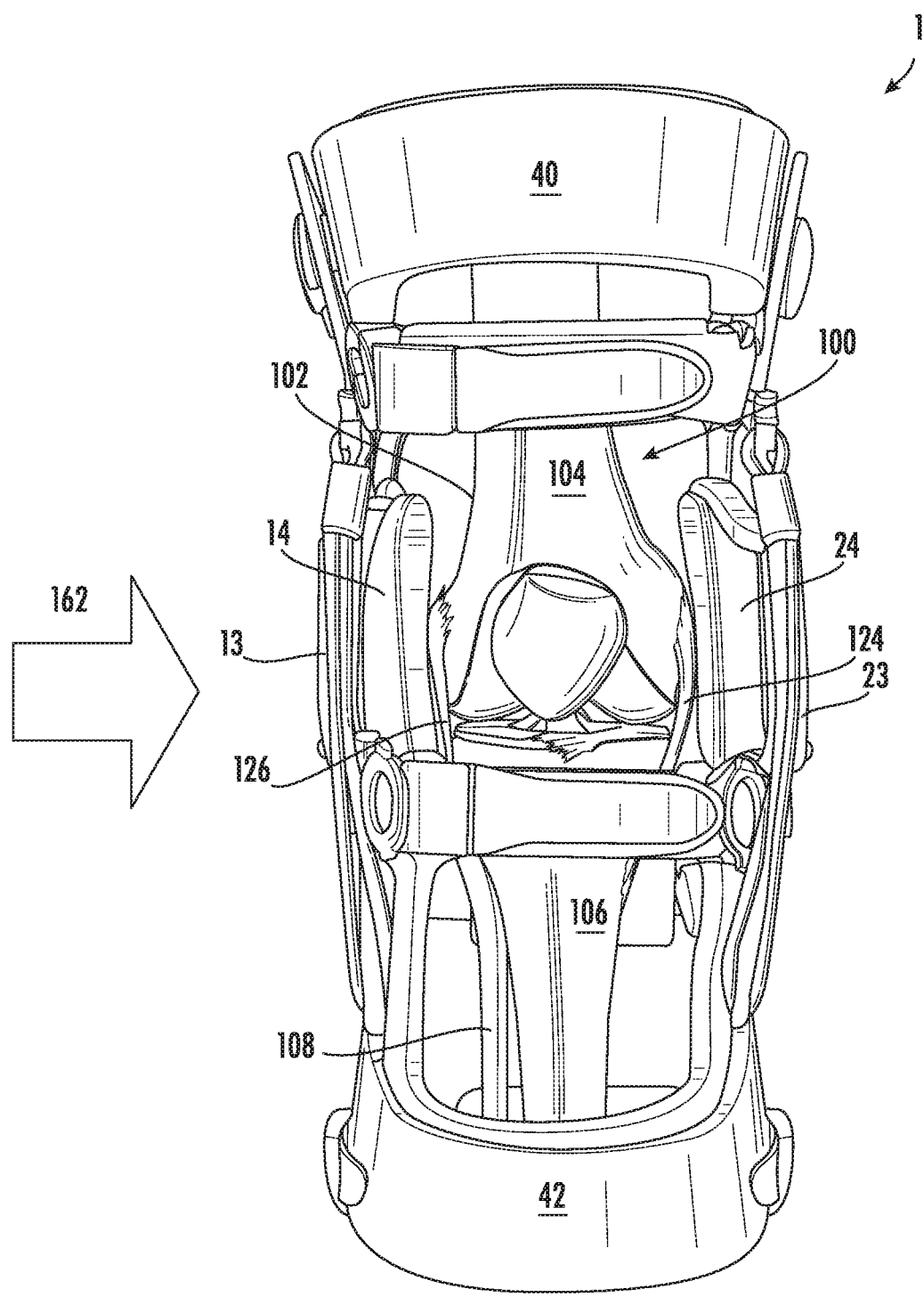
FIG. 8 illustrates a knee within the device for protecting a knee from external forces.

Referring to FIG. 8, a knee within the device for protecting a knee from external forces is shown.

With the lower leg 100 and knee 102 surrounded by the force dissipation brace 1, the knee 102 is protected against a lateral force 162. An external force, such as lateral force 162, contacts the lateral hinge 13. The force is spread from the lateral hinge 13 to the lateral strut 10, up and down to the anterior thigh cuff 40 and anterior shin cuff 42. Deformation of the lateral strut 10 causes compression of the lateral bladder 14, which cyclically compresses and decompresses, absorbing the incoming force.

Finally, any force that is passed to the knee 102 causes compression of the opposite bladder, or here the medial bladder 24, preventing excessive stretching of the MCL 124, which could cause tearing.

Figure 9:
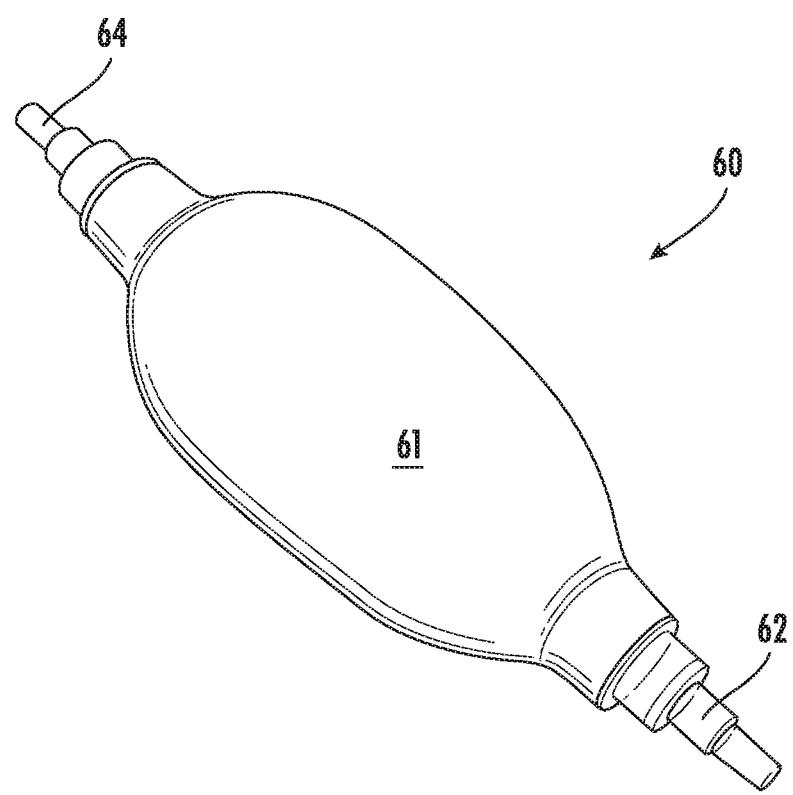
FIG. 9 illustrates an inflation pump for the device for protecting a knee from external forces.

Referring to FIG. 9, an inflation pump for the device for protecting a knee from external forces is shown.

The body 61 of the pump 60 is formed from a compressible, resilient, and air-tight material. Compression of the body 61 pushes air out of the discharge nozzle 64. The body 61 then self-inflates, drawing air in through the suction nozzle 62.

The pump 60 is used to add and remove air from the lateral bladder 14 and medial bladder 24.

Equivalent elements can be substituted for the ones set forth above such that they perform in substantially the same manner in substantially the same way for achieving substantially the same result.

It is believed that the system and method as described and many of its attendant advantages will be understood by the foregoing description.

It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A method of protecting a human knee of a lower leg from external forces, the method comprising the steps of:
    surrounding the lower leg with a force dissipation brace comprising:
        a lateral air bladder on a side of the human knee;
        a medial air bladder on an opposite side of the human knee;
            the lateral air bladder and medial air bladder each including an inlet/outlet nozzle to permit adjustment of internal air pressure;
            the internal air pressure of the lateral air bladder and medial air bladder affecting the behavior of the lateral air bladder and medial air bladder with respect to external forces;
            the lateral air bladder held in place by the combination of:
                a lateral strut divided by a lateral hinge;
            the medial air bladder held in place by the combination of:
                a medial strut divided by a medial hinge;
            the lateral strut connected to the medial strut by an anterior thigh cuff and an anterior shin cuff;
            the lateral strut and medial strut enclosing the lower leg with an anterior thigh strap, an anterior shin strap, a posterior thigh strap, a posterior upper shin strap, and a posterior lower shin strap;
    tightening the anterior thigh strap, anterior shin strap, posterior thigh strap, posterior upper shin strap, and posterior lower shin strap to hold the lower leg within the force dissipation brace;
    inflating the medial air bladder to compress the force dissipation brace against the human knee;
    inflating the lateral air bladder to compress the force dissipation brace against the human knee;
    additionally inflating the medial air bladder to further compress the force dissipation brace against the human knee;
    additionally inflating the lateral air bladder to further compress the force dissipation brace against the human knee;
    exposing the brace to an external force;
        the external force applied to the medial strut;
        the external force spreading up and down the medial strut, causing deformation of the medial strut;
        the deformation of the medial strut causing deformation of the medial bladder;
        the deformation of the medial bladder causing the medial bladder to pass through a cycle of absorbing, dissipating, and spreading the force of impact;
    whereby the human knee is protected from injury.

2. The method of claim 1, further comprising the step of:
    inflating the lateral air bladder more than the medial air bladder, thereby opening a medial side of the human knee.

3. The method of claim 1, further comprising the step of:
    inflating the medial air bladder more than the lateral air bladder, thereby opening a lateral side of the human knee.

4. The method of claim 1, wherein the brace further comprises:
    a medial guide channel crossing the medial hinge;
        a medial elastic member connecting the medial strut across the medial hinge;
            the medial elastic member causing the medial strut to move toward a straight position and away from a bent position;
            thereby encouraging unbending of the human knee;
    a lateral guide channel crossing the lateral hinge;
        a lateral elastic member connecting the lateral strut across the lateral hinge;
            the lateral elastic member causing the lateral strut to move toward a straight position and away from a bent position;
            thereby encouraging unbending of the human knee.

5. The method of claim 1, wherein the step of exposing the brace to an external force further comprises the step of:
    the external force causing motion of the human knee that causes compression of the lateral air bladder.

6. A method of protecting a human knee of a lower leg from external forces, the method comprising the steps of:

surrounding the lower leg with a force dissipation brace comprising:
- a lateral air bladder on a side of the human knee;
- a medial air bladder on an opposite side of the human knee;
  - the lateral air bladder and medial air bladder including an inlet/outlet nozzle to permit adjustment of internal air pressure;
  - the internal air pressure of the lateral air bladder and medial air bladder affecting the behavior of the lateral air bladder and medial air bladder with respect to external forces;
- the lateral air bladder held in place by the combination of:
  - a lateral strut divided by a lateral hinge;
- the medial air bladder held in place by the combination of:
  - a medial strut divided by a medial hinge;
- the lateral strut connected to the medial strut by an anterior thigh cuff and an anterior shin cuff;
- the lateral strut and medial strut enclosing the lower leg with an anterior thigh strap, an anterior shin strap, a posterior thigh strap, a posterior upper shin strap, and a posterior lower shin strap;
- a medial guide channel crossing the medial hinge;
  - a medial elastic member connecting the medial strut across the medial hinge;
    - the medial elastic member causing the medial strut to move toward a straight position and away from a bent position;
    - thereby encouraging unbending of the human knee;
- a lateral guide channel crossing the lateral hinge;
  - a lateral elastic member connecting the lateral strut across the lateral hinge;
    - the lateral elastic member causing the lateral strut to move toward a straight position and away from a bent position;

tightening the anterior thigh strap, anterior shin strap, posterior thigh strap, posterior upper shin strap, and posterior lower shin strap to hold the lower leg within the force dissipation brace;

inflating the medial air bladder to compress the force dissipation brace against the human knee;

inflating the lateral air bladder to compress the force dissipation brace against the human knee;

additionally inflating the medial air bladder to further compress the force dissipation brace against the human knee;

additionally inflating the lateral air bladder to further compress the force dissipation brace against the human knee;

exposing the brace to an external force;
- the external force applied to the medial strut;
- the external force spreading up and down the medial strut, causing deformation of the medial strut;
- the deformation of the medial strut causing deformation of the medial bladder;
- the deformation of the medial bladder causing the medial bladder to pass through a cycle of absorbing, dissipating, and spreading the force of impact;

whereby the human knee is protected from injury.

7. The method of claim 6, further comprising the step of:
inflating the lateral air bladder more than the medial air bladder, thereby opening a medial side of the human knee.

8. The method of claim 6, further comprising the step of:
inflating the medial air bladder more than the lateral air bladder, thereby opening a lateral side of the human knee.

9. The method of claim 6, further comprising the step of:
the external force causing motion of the human knee that causes compression of the lateral air bladder.

* * * * *